United States Patent [19]

Fresnel et al.

[11] 4,016,044

[45] Apr. 5, 1977

[54] METHOD AND APPARATUS FOR GOVERNING THE REACTION RATE OF ENZYMATIC REACTIONS

[75] Inventors: Jean-Marie Fresnel, Haut-Thoiry, France; Daniéle Trosset, Carouge, Switzerland

[73] Assignee: Battelle Memorial Institute, Switzerland

[22] Filed: May 29, 1975

[21] Appl. No.: 581,761

Related U.S. Application Data

[63] Continuation-in-part of Ser. No. 431,608, Jan. 8, 1974, Pat. No. 3,919,052.

[30] Foreign Application Priority Data

Jan. 10, 1973  Switzerland ........................ 259/73
Jan. 10, 1973  Switzerland ........................ 260/73

[52] U.S. Cl. ............................. 195/115; 195/116; 195/127; 204/1 T; 204/195 B
[51] Int. Cl.$^2$ ............................................ C12B 1/00
[58] Field of Search ............ 195/31, 63, 103.5, 68, 195/115, 116, 104, 108, 117–118, DIG. 1, 127; 204/195 B, 195 T, 1 E, 1 R

[56] References Cited

UNITED STATES PATENTS

| 3,542,662 | 11/1970 | Hicks et al. ................ 195/103.5 R |
| 3,623,960 | 12/1973 | Williams ...................... 204/195 P |
| 3,753,725 | 8/1973 | Williams et al. .................. 195/104 |
| 3,776,819 | 11/1971 | Williams ...................... 204/195 B |
| 3,919,052 | 11/1975 | Fresnel et al. .................... 195/115 |

*Primary Examiner*—R. B. Penland
*Attorney, Agent, or Firm*—Robert E. Burns; Emmanuel J. Lobato; Bruce L. Adams

[57] ABSTRACT

Heterogeneous enzymatic catalysis is carried out by means of an enzymatic electrode comprising an enzyme fixed to a solid, conductive support. To govern the reaction rate during continuous transformation of a substrate, the enzymatic activity is regulated by adjusting the potential of the enzyme support so as to transform the substrate at a given rate. The electrode is provided with a particulate enzymatic mass operatively associated with an inert working electrode for contact with this mass to thereby subject the particles thereof to the adjustable potential. Continuous movement of a liquid reaction system is produced so as to provide intimate contact thereof with each particle of the mass, which may be arranged as a fixed bed, an agitated bed or a fluidized bed. The potential of the enzyme support is caused to continually alternate between two levels while adjusting the mean value thereof so as to maintain a corresponding mean enzymatic activity for transforming the substrate at the desired rate.

14 Claims, 4 Drawing Figures

METHOD AND APPARATUS FOR GOVERNING THE REACTION RATE OF ENZYMATIC REACTIONS

This application is a continuation-in-part of our earlier copending application, Ser. No. 431,608 filed Jan. 8, 1974 now U.S. Pat. No. 3,919,052.

The invention relates to the field of heterogeneous enzymatic catalysis and in particular to a method of governing the reaction rate of enzymatic reactions for industrial transformation processes.

In our prior pending application identified above there has been disclosed a method and apparatus for governing the reaction rate of enzymatic reactions wherein a substrate is continuously transformed by contact with an enzyme fixed to a solid carrier.

The method of our said prior application comprises the steps of:

a. providing an enzymatic electrode with at least one enzyme fixed to a solid electronically conductive enzyme support;

b. contacting a liquid reaction medium containing the substrate to be transformed with said enzymatic electrode; and c. regulating the catalytic activity of said enzyme by applying a potential to said electrode while adjusting the value of said potential in such a manner as to transform said substrate at a substantially uniform rate.

The possibility of thus effecting enzymatic electrocatalysis to regulate the catalytic activity of an enzyme, by adjusting the electric potential of its conductive support according to the said method, provides a number of technical advantages which are of great practical significance for carrying out any industrial process wherein enzymatic catalysis may be utilized.

Thus, the great selectivity of each enzyme for transforming a given substrate constitutes, a priori, a major asset of all enzymes. On the other hand, the catalytic activity of an enzyme, which is evidently a determining factor with regard to the reaction rate, essentially presents an impredictable character since the activity may vary quite considerably in the course of time and moreover depends on various factors which, in turn, tend to vary more or less independently of each other. Consequently, the said possibility of regulating the catalytic activity, solely by means of the potential of the enzyme support, is particularly significant in as much as it enables the simultaneous compensation of the influence of various factors which are difficult to control in the best of cases and are practically impossible to control in many cases.

Now it is evident that the application of enzymatic catalysis on an industrial scale must meet a number of technical requirements which differ substantially from those of enzymatic reactions carried out on a small scale, in a batch process, for example on a laboratory scale.

Thus, for example, the proportion of enzyme which is effectively used for catalysis, the overall efficiency and reproducibility of the process, the complexity and cost of apparatus used, the possibility of ensuring more or less continuous operation and the necessity of utilizing highly qualified operators, may all constitute determining factors for the efficient and economic exploitation of an industrial process.

The possibility of rapid and precise governing of the reaction rate via the potential of the enzymatic electrode is thus evidently of great interest in this regard.

However, the use of an enzymatic electrode comprising a unitary electrode body, as described in our said copending application, provides a correspondingly limited area for contact of the substrate with the enzyme fixed to the external surface of the said electrode body. Moreover, the amount of enzyme which may be fixed at said external surface, per unit volume of said solid unitary electrode body, is also correspondingly limited by said area. In addition, truly efficient use of the enzyme fixed to the enzymatic electrode necessitates intimate contact of the whole liquid reaction system containing the substrate with the whole enzyme fixed to this electrode.

The general object of the present invention is more fully achieve the advantages which are inherent in regulating the enzymatic activity by carrying out enzymatic electrocatalysis, as described in our said copending application, so as to more fully meet the above mentioned requirements of an industrial process.

One object of this invention is to provide a method which largely obviates the above mentioned limitations. To this end, the following improvements are provided in accordance with this invention:

an enzymatic electrode is provided with a particulate enzymatic mass, composed of discrete enzymatic particles each formed of a solid, conductive support having the desired enzyme fixed to the surface thereof, and with a solid inert working electrode operatively associated with said enzymatic mass so as to subject said mass to an adjustable potential;

the liquid reaction system containing the substrate to be transformed is circulated through a reaction chamber so as to produce relative movement thereof with respect to said enzymatic electrode and to thereby provide intimate contact with each particle of said enzymatic mass; and an adjustable potential is applied to said working electrode, in such a manner as to subject the particles of said enzymatic mass to said potential and to thereby regulate the catalytic activity of said enzyme.

In accordance with this invention, an apparatus is further provided for carrying out this improved method. This apparatus essentially comprises the following improvements:

the apparatus includes at least one enzymatic electrode comprising a particulate enzymatic mass, compound of discrete enzymatic particles each formed of a solid, conductive support having the desired enzyme fixed thereto, and further comprising a solid inert working electrode operatively associated with said mass and with an adjustable electric supply and voltage control means so as to subject the particles of said mass to an adjustable potential; and the apparatus further comprises circulating means adapted to circulate a liquid reaction system, containing the substrate to be transformed, within a reaction chamber, including said enzymatic electrode associated with a solid inert counter-electrode, in such a manner as to provide intimate contact of said liquid reaction system with each particle of said enzymatic mass, the particles of said mass being subjected to said adjustable potential during said circulation.

By thus providing an enzymatic electrode with such a particulate enzymatic mass, the amount of fixed enzyme which may be used for enzymatic electrocatalysis can be considerably increased, as well as the surface which is available for contact between this enzyme and the liquid reaction medium containing the substrate to be transformed. Moreover, as will be seen hereinafter, the enzymatic particles may be readily subjected to an adjustable potential by direct or indirect contact with the said inert working electrode.

In addition, the said circulation of the liquid reaction system readily provides optimal intimate contact thereof with the total large surface of the particulate mass of the enzymatic electrode and hence with the whole enzyme fixed thereon.

Moreover, the duration of contact between the enzyme fixed to the particles of the enzymatic mass and the substrate to be transformed may be readily adjusted by adjustment of the speed of said circulation.

It thus becomes possible to achieve enzymatic electrocatalysis under substantially improved conditions in a simple apparatus which has minimal space requirements.

An appropriate adjustment of the potential applied to the said working electrode thus allows the substrate to be transformed at a substantially uniform rate by means of the enzyme fixed to the particulate enzymatic mass subjected to said potential.

The present invention is further directed to improvements based on interesting phenoma which applicants have discovered during their further investigations of the enzymatic electrocatalysis effect:

It has been found by a series of experiments that when a maximum enzymatic activity is reached by applying an appropriate constant potential to a fixed enzymatic electrode, the activity thereafter tended to diminish quite rapidly so as to more or less annul the effect of said potential. In other words, the maintenance of maximum activity does not seem possible when the conductive enzyme support is subjected to a constant potential. This clearly demonstrates the particular significance of adjusting the potential of the enzymatic electrode so as to be able to maintain an optimum, relatively high mean enzymatic activity, as is provided for in accordance with applicants method, as opposed to providing maximum activity which cannot be sustained for a sufficient period of time to be of practical significance.

In addition, another phenomenon has been experimentally established, namely, that an alternating variation of the potential of the enzyme support, around an adjustable mean potential, enables a much higher mean catalytic activity to be maintained than when the enzyme is subjected to the action of a constant potential.

It is thus another object of the present invention to provide an improved method which exploits the above mentioned phenomena.

To this end, the following improvement is further provided in accordance with this invention: the potential of the solid, conductive enzyme support is caused to continually alternate between two levels while adjusting the mean value thereof in such a manner as to maintain a corresponding mean catalytic activity of the enzyme whereby to transform said substrate at the desired rate.

In accordance with a preferred variant of this improvement, an enzymatic electrode is provided with a particulate enzymatic mass associated with a working electrode and the liquid is circulated through a reaction chamber, both substantially as already set forth hereinbefore, while the enzymatic particles of said mass are alternately brought to said two potential levels whereof the mean value is adjusted.

By thus providing an enzymatic electrode formed of two distinct parts (one catalytically active, the other conductive and inert), one may readily select quite different types of arrangements for the two parts of this electrode so as to be able to fulfill these two functions of support and potential adjustment under the best conditions for each application which is envisaged.

An important advantage obtained in all cases resides in the fact that, as opposed to a solid unitary electrode bearing the enzyme on its external surface only, a mass of discrete enzymatic particles enables a much higher enzyme fixation ratio (enzyme / support by weight) and a much larger active surface to be achieved in the enzymatic electrode. Moreover, as will be seen further below, it becomes possible to utilize different types of reactors allowing enzymatic catalysis to be achieved in a most efficient way.

Thus, for example, when a fixed packed bed of enzymatic particles is utilized in contact with the solid, inert working electrode, the specific active electrode surface is evidently several times higher than that of a consolidated enzymatic electrode body. However, since the liquid reaction system must pass through the entire packed bed, this bed must be formed of relatively large particles or granules in order to avoid the well known phenomenon of channel, i.e. preferential flow through one part of the bed only. Moreover, the liquid flow velocity through the bed must be limited so as to avoid an excessive pressure drop.

On the other hand, one may advantageously utilize an electrode of the dispersed type where the enzymatic particles undergo intermittent contact with the working electrode, said contact then being obtained by a relative movement which may be achieved in different ways such as by: a mechanically agitated bed, a fluidized bed or a circulating bed in suspension.

The agitated bed provides intimate and prolonged liquid / solid mixing, thus promoting the delivery of substrate to the reaction site and the distribution of the reaction products in the bulk of the liquid.

On the other hand, a fluidized bed, as well as a fixed packed bed, enables the reaction products to be continuously discharged out of the bed and this may constitute a very important advantage with regard to reactions whereof the product constitutes a competitive inhibitor capable of hindering the reaction from proceeding.

As regards the circulating bed, it enables the amount of particulate enzymatic mass to be increased practically at will, as well as the number of contacts thereof with the working electrode, particularly due to recycling.

The accompanying drawing illustrates schematically and by way of example, several embodiments of an apparatus for carrying out the improvements in accordance with the present invention.

Figure 1:
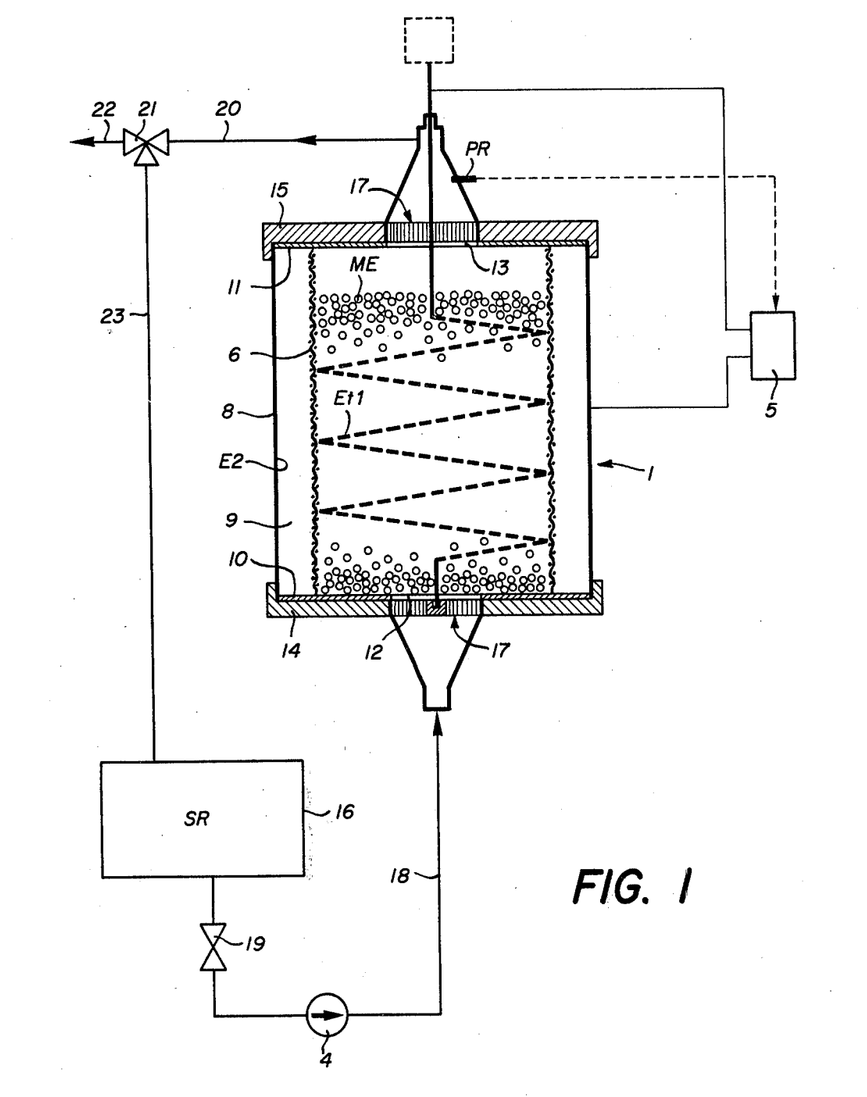
FIG. 1 is a schematic vertical cross-section of a first embodiment, which comprises a fixed bed.

The apparatus shown in FIG. 1 essentially comprises a cylindrical reactor 1, a circulating pump 4 with adjustable throughput, a reservoir 16 for the liquid reaction system SR containing the substrate to be transformed and an electric supply source 5 adapted to supply an adjustable potential.

A major part of the reaction 1 consists of a reaction chamber which is laterally defined by a porous partition 6 and encloses an enzymatic electrode EE comprising a mass ME of enzymatic particles, consisting of conductive granules having the enzyme fixed thereon, and an inert working electrode $Et1$ arranged in contact with said mass of particles. A metallic outer wall 8 is coaxially arranged around the partition 6 and defines therewith an annular compartment 9 surrounding the reaction chamber. This wall 8 at the same time forms an inert counter-electrode E2 connected to one terminal of the source 5 while the working electrode $Et1$ is connected to another terminal of the source.

The top and bottom ends of the reactor 1 are respectively defined by internal insulating plates 10 and 11 between which the wall 8 and the partition 6 are coaxially mounted. The bottom plate 10 has an axial inlet 12 for the liquid SR to be treated and the top plate 11 has an outlet 13 for the liquid having undergone treatment in the reaction chamber. These plates 10 and 11 are respectively covered with outer insulating plates 14 and 15. Porous elements 17 are arranged in the middle of the outer plates 14 and 15 respectively facing the orifice 12 of the plate 10 and the orifice 13 of the plate 11, so as to allow circulation of the liquid through the reaction chamber while retaining the said granules of the enzymatic electrode EE.

The reaction chamber is connected on one hand to the reservoir 16 via a feed conduit 18 communicating with the inlet 12, through the porous element 17. A value 19 and the pump 4 are mounted in this conduit 18 so as to allow continuous, adjustable supply of the reactor with liquid SR to be treated, from the reservoir 16.

On the other hand, the reaction chamber is connected to a discharge conduit 20 communicating with the outlet 13 via the porous element 17. A three-way valve 21 is associated with this conduit 20 so as to direct the treated liquid either towards a conduit 22 leading to a storage reservoir (not shown) or to any other desired place, for example to a subsequent treatment stage, or towards a conduit 23 for returning the treated liquid to the reservoir 16 and, consequently, for achieving repeated treatment of the same liquid in the reactor 1.

A measuring instrument PR is further arranged at the outlet of the reactor 1 so as to measure a physical or chemical variable of the treated liquid and to control the potential source 5, as is schematically indicated by dashed lines in FIG. 1.

The working electrode $Et1$, indicated schematically by dash-dotted lines, is mounted in the reaction chamber and may be formed of a grid bent in zig-zag shape and arranged so that it presents a very large surface for contact with the granules enclosed in the reaction chamber. This allows a good direct or indirect electrical contact to be ensured between this electrode $Et1$ and these granules so that more or less the whole mass of granules may be brought at the same time to a given electric potential.

The enzyme serving to catalyze the reaction intended to effect the desired transformation in the liquid coming from the reservoir 16, is fixed on each of the said granules which are formed in the present case of graphite having a mean grain size lying between 100 $\mu$ and 400 $\mu$.

This fixation of the enzyme may be achieved in any appropriate manner, for example by means of a polymerization allowing the enzyme to be fixed via a covalent bond with a polymer formed on the conductive support of graphite and adhering thereto.

A particulate mass for use in the enzymatic electrode may be prepared in the following manner:

A support in the form of particulate graphite is first subjected to a chemical oxidation by contact with a mixture of potassium permanganate and sulphuric acid. This oxidation produces functional groups of the carboxyl, ketone, quinone or lactone types on the surface of the graphite.

The support thus oxidized is activated by means of Woodward K reagent and then contacted with an aqueous solution of the enzyme which is thereby fixed by means of a covalent bond betwen the activated carboxylic groups of the graphite and the amino groups of the enzyme.

It is understood that the structural details of the above described reactor are not shown in the schematic cross-section of the drawing, FIG. 1. It may thus be noted that this reactor is constructed so as to permit rapid assembly and disassembly to thereby facilitate periodic cleaning of the reactor and replacement of the particulate mass ME of the enzymatic electrode. To this end, the partition 6 and the plates 10 and 11, which enclose the enzymatic electrode, may be arranged so that they constitute a reaction chamber in the form of a removable cartridge. This allows a considerable shortening of the stopping time for the operations of cleaning, disinfection, and regeneration or replacement of the enzymatic mass. Indeed, such a cartridge may be readily and rapidly replaced by a spare cartridge in order to allow approximately uninterrupted operation of the reactor and, if need be, a rapid transition from one type of enzymatic catalysis to another.

The reactor described above with reference to FIG. 1 may be used to carry out the process according to the present invention in the following manner:

After having selected the appropriate enzyme for catalyzing the desired reaction and having fixed this enzyme on the conductive graphite granules, the reaction chamber is filled with a mass of these granules to constitute therein the enzymatic electrode composed of a bed of these granules arranged in contact with the control electrode $Et1$.

The liquid reaction system SR to be treated and containing the substrate to be transformed in the reactor 1 is then introduced into the reservoir 16. If the liquid SR to be treated does not have the appropriate initial composition, ionic strength, pH and temperature which are necessary to carry out the desired reaction by enzymatic electrocatalysis in the reactor 1 in a truly satisfactory manner, it is first prepared so as to obtain an appropriate reaction system, for example, by adding substances permitting to obtain the desired pH and ionic strength, and by heating the reaction system to the desired reaction temperature. If necessary, the reservoir 16 may be provided with a thermal insulation, or maintained at a constant temperature by means of a thermostat (not shown), or both.

Moreover, certain variations of the pH and the temperature, among other reaction parameters, can be compensated by means of an appropriate adjustment of the electrode potential as is described further on.

To carry out the desired enzymatic reaction, the valves 19 and 21 are first opened and the pump 4 is actuated so as to cause the liquid SR to be treated to circulate through the reaction chamber. The porous partition 6 being permeable to the liquid, the annular chamber 9 is likewise filled with this liquid so as to establish an electric circuit consisting of the source 5, the working electrode E$t$1, the mass ME of enzymatic granules, the liquid situated in the reactor 1, and the counter-electrode 8.

The working electrode E$t$1 and the counter-electrode 8 are respectively connected to two terminals of the source 5 so as to apply an adjustable potential difference serving to establish an electric field across the liquid in the reactor and to thus bring the enzymatic electrode to a given potential level with respect to the liquid which circulates through the reaction chamber, in contact with the said mass of granules ME. The activity of the enzyme fixed to the granules may thus be governed by adjusting this potential level, so that the enzymatic reaction can be made to proceed at the desired rate.

Some preliminary tests, for each reaction which is envisaged, will allow the ranges of potential difference and the circulation rates to be determined which are suitable for carrying out the desired reaction in a correct manner.

Now, the measuring instrument PR allows continuous monitoring of the treated product leaving the reactor to control whether it has undergone the desired transformation and to govern the potential supply source 5, as a function of this measurement, in such a manner as to obtain a treated product of uniform quality. The measurement obtained by this instrument PR may be utilized, if need be, to likewise control the actuation of the valves 21 and 19 and of the pump 4, or both.

According to a variant of the described reactor, the latter may be equipped with a working electrode E$t$1 to which a rotating movement is imparted by means of a motor which is represented schematically in dotted lines at the top of FIG. 1.

In the enzymatic electrode utilized in accordance with the present invention, the granules used to constitute the conductive enzyme support may have any appropriate size, in the range from 0.1–1.5 mm, for example. Instead of granules, one may likewise utilize, as an enzyme support, graphite fibers, with a diameter of 10 $\mu$ for example, and with any desired length which may go up to several centimeters, for example up to 10 cm.

It is likewise understood that the granules or fibers may formed of any other material than graphite, so long as it permits fixation of the enzyme thereon, that it has a good electric conductivity and that it is sufficiently inert chemically and electrochemically with regard to the reaction system as well as to the enzyme fixed thereon. Thus, for example, the granules or fibers may be formed of any other carbon-based material or even of metals or alloys which are chemically and electrochemically inert.

It is evident that the important advantages which are obtained thanks to the method of the present invention are not limited to particular enzymatic reactions. Indeed, the invention may be applied to any desired enzymatic reaction by selecting the appropriate enzyme to be fixed in each case on the granules or fibers of the conductive enzyme support of the enzymatic electrodes.

Thus, for example, the method of the present invention may be carried out by means of the described apparatus to carry out a continuous, controlled delactosation of deproteinized lactoserum supplied from the reservoir 16, by an enzymatic reaction to effect hydrolysis and transformation of the lactose into glucose and galactose, in the reactor 1.

To this end, an enzymatic electrode may be utilized comprising the enzyme lactase fixed to the conductive granules (of graphite) so as to control the course of the said enzymatic electrode. The proportion of converted lactose is then greater than 85 % of the initial lactose. One may moreover utilize a measuring instrument PR in the form of a known type of glucose oxydase measuring electrode, in order to measure the amount of formed glucose present in the treated liquid leaving the reactor. The delactosation rate may be maintained at a desired uniform value by acting on the potential of the enzymatic electrode, as a function of the said measurement.

Figure 2:
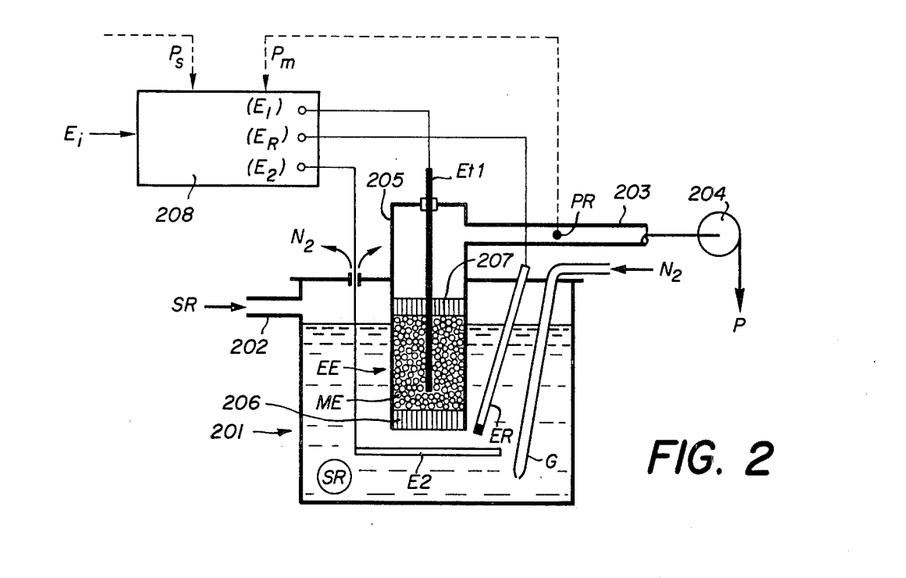
FIG. 2 is a schematic vertical cross-section of a second embodiment, which comprises a fixed bed.

The apparatus of FIG. 2 comprises a reaction cell 201 containing an enzymatic electrode EE, a reference electrode ER and an inert counter-electrode E2 (of platinum). A liquid supply source (not shown) delivers the liquid reaction system SR to an inlet 202 of the cell 1 wherein it forms a bath and then follows the enzymatic electrode EE, wherefrom the liquid P containing the reaction product is discharged through an outlet 203 by means of a suction pump 204 having an adjustible throughput.

The electrode EE comprises an enzymatic mass ME arranged in contact with a control electrode E$t$1 within a glass tube 205. This electrode E$t$1 is formed of an inert material (graphite) and the said mass ME constitutes a fixed, porous bed composed of packed enzymatic particles pe each formed of a conductive support (graphite) on which the enzyme is fixed by a covalent bond in any appropriate manner, such as is described above. This fixed bed ME is arranged within the tube 205 between two porous plates 206 and 207.

The electrode ER may be, for example, a standard saturated calomel electrode (SCE). A tube G further serves to bubble an inert protective gas ($N_2$) through the bath of liquid SR situated in the cell 1.

The three electrodes E$t$ 1, ER and E2 are connected to an electric supply source 208. This source comprises a potentiostat associated with a repeated pulse generator (chopper) so as to apply to the control electrode E$t$1 an adjustable potential $E_t$ in the form of a series of periodic pulses.

This supply source 208 is arranged to allow, on one hand, adjustment of the initial mean value $E_i$ of the potential pulses applied to the electrode with respect to the reference electrode ER (SCE). This initial value $E_i$/SCE may be determined without difficulty by means of a few preliminary tests in which the desired enzymatic reaction is carried out at approximately the reaction conditions foreseen for normal operation of the apparatus.

This source 208 is on the other hand arranged so as to allow adjustment of the mean value of the potential $E_t$ as a function of the difference between a set value $P_s$ and an instantaneous measured value $P_m$ of an output variable which depends on the reaction rate and corresponds to the reaction product P obtained at the outlet 203.

A measuring instrument PR has been schematically indicated which is arranged in the outlet 203 and is intended to deliver to said measured value $P_m$ so as to allow adjustment of the potential $E_t$ as a function of $P_m$, by means of the electric supply source 208, as is indicated in broken lines.

As a matter of fact, the described apparatus, equipped with such an instrument PR, allows adjustment of the potential $E_t$ and, consequently, of the activity of the enzyme fixed on the enzymatic electrode, so as to enable maintenance of the said input variable at its desired value, by eliminating any divergence which appears between $P_m$ and $P_s$ in the course of the reaction. In other words, one may quite easily obtain a closed-loop regulation enabling maintenance of $P_m$ equal to $P_s$. It thus becomes possible to achieve through relatively simple means, a closed-loop automatic regulation system comprising the source 208, the cell 201 and the measuring instrument PR.

The apparatus described above and shown in FIG. 2 may be utilized to effect electrocatalysis in the following manner:

a. The enzyme is first selected according to the substrate to be transformed through the enzymatic electrode EE. The enzymatic mass of this electrode is then prepared by fixing this enzyme on graphite granules with a mean size of the order of 1,500 $\mu$, for example. This fixation may be achieved in any appropriate manner and in particular by means of a covalent bond between the enzyme and reactive groups formed by pretreatment of the graphite support. Various fixing techniques may be envisaged which will not be described in greater detail since they do not form a part of the improvements according to the present invention.

b. After mounting the electrodes in the apparatus according to the arrangement of FIG. 2, the pump 204 is actuated to circulate the reaction liquid SR at a given flow rate; the mean composition of the liquid SR is determined beforehand, as well as the optimal flow rate through the apparatus, which may moreover operate at different flow rates.

c. After having set the frequency and the amplitude of the potential pulses, as well as the initial mean potential $E_t$ and the set value $P_s$, on the source 208 connected to the electrodes E$t$1, E2 and ER, the desired reaction will proceed by enzymatic electrocatalysis within the enzymatic electrode EE; the activity of the enzyme is then adjusted in the course of the reaction by continually effecting adjustment of the mean potential $E_t$ applied by the source 208 to the electrode EE via the working electrode thereof.

d. In order to main a desired reaction rate one proceeds with the control in the following manner:

the instrument PR associated with the outlet 203 (FIG. 2) is utilized to continuously or intermittently measure in the course of the reaction, the instantaneous value $P_m$ of the output previously mentioned, which corresponds to the reaction product;

$P_m$ is continually compared to $P_s$ in order to determine every difference $\epsilon$ which appears between them and $E_t$ is adjusted as a function of this difference $\epsilon$, by increasing $E_t$ when $P_m$ is less than $P_s$ and vice versa, so that this divergence $\epsilon$ is continually annulled as soon as it appears in the course of the reaction so that the reaction thus proceeds at a mean rate corresponding to the set value $P_s$.

This apparatus thus enables a substantially constant mean catalytic activity to be maintained by adjusting the potential $E_t$ applied by the source 208 to th enzymatic electrode EE.

Now, this apparatus may be readily adapted for automatic operation with a closed-loop regulation system comprising the source 208, the cell 201 and the measuring instrument PR associated with conventional means (comparator, etc.) capable of producing an error signal $\epsilon = P_s - P_m$ and of controlling $E_t$ automatically as a function of this error.

It thus becomes possible, thanks to this apparatus according to FIG. 2, to simultaneously compensate the influence of various variable factors, such as pH, temperature of the reaction system and the diminution of activity which may have different causes such as the inhibition, poisoning or aging of the enzyme.

Moreover, the apparatus used to this end is relatively simple, as appears from the preceding description. The source 208 and the measuring instrument PR may be formed of conventional components which have not been described in greater detail since they do not constitute a part of the improvements provided for in accordance with the present invention.

It is evident, however, that adjustment of the potential $E_t$ will enable compensation of variations of the reaction parameters (e.g. pH, temperature only within certain limits. Thus, for example $E_t$ may evidently not be increased at will since the passage of an excessive current through the liquid reaction system may lead to excessive heating which may gravely affect the activity of the enzyme, so that the current must be limited accordingly.

Moreover, the adjustable potential $E_t$ applied to the electrode EE must evidently be maintained within a range enabling a satisfactory level of activity to be achieved.

Now, various ranges of control of the potential $E_t$ may be readily established experimentally for the apparatus operating at different flow rates of the reaction liquid SR. One may thus select the most appropriate flow rate to ensure adjustment of the potential $E_t$ within the limits which permit the enzymatic activity to be maintained at a satisfactory value.

Figure 3:
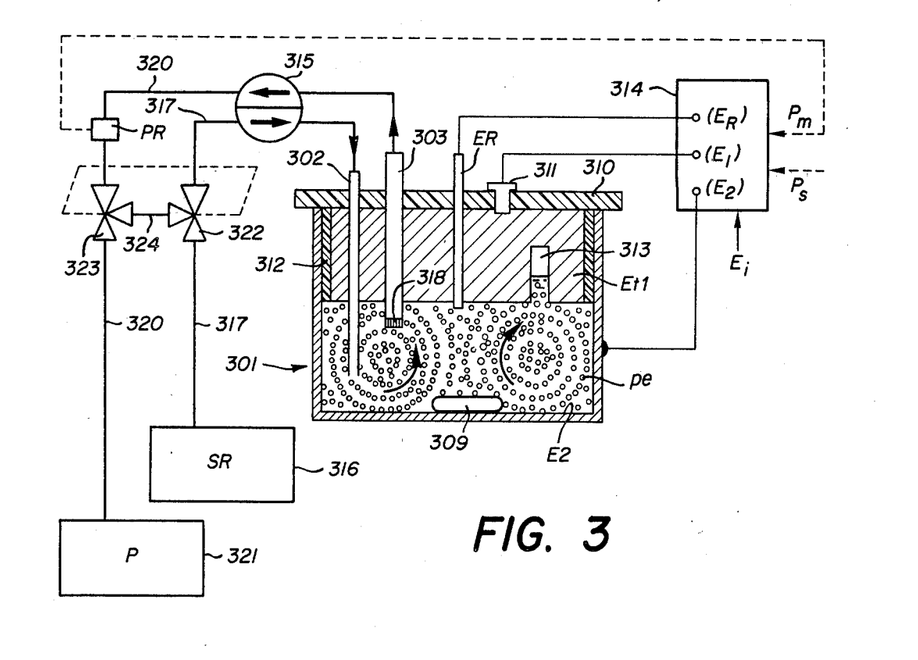
FIG. 3 is a schematic vertical cross-section of a third embodiment which comprises an agitated bed.

In the embodiment shown in FIG. 3, the apparatus likewise comprises a reaction cell 301 provided with an inlet 302, an outlet 303 and an enzymatic electrode EE associated with a reference electrode ER (of the SCE type) and a counter-electrode E2.

However, the electrode arrangement is quite different. Thus the enzymatic electrode EE here comprises a mass ME of enzymatic particles pe which are put in suspension in the liquid reaction system SR so as to form an agitated bed which is mechanically agitated by means of a stirrer 309.

This agitated bed is enclosed between the counter-electrode E2, here formed by the wall (of vitreous carbon) of the reaction cell 301, and the control electrode E$t$1, here formed by a massive block of graphite. This block is fixed to an insulating cover 310, connected to a terminal 311 and insulated from the wall (electrode E2) of the vessel 301 by means of an insulating packing 312.

The massive electrode E$t$1 thus presents its bottom surface for contact with the said agitated bed and is traversed by the inlet 302, the outlet 303 and the reference electrode ER which is surrounded by a glass sleeve (not shown). The massive block E$t$1 further comprises a cavity 313 which communicates with the cell 1 and constitutes a buffer volume which enables the bottom surface of the electrode E*t*1 to be maintained in permanent contact with the said agitated bed.

The stirrer is schematically represented by its agitating member 309 which is actuated from outside the cell by means of a magnetic field, in such a manner as to impart to the whole agitated bed a vertical circulating movement such as indicated by arrows; this movement thus produces repeated collisions between the particles pe in suspension in the agitated bed and, on one hand, the bottom surface of the electrode E*t*1 and, on the other hand, the counter-electrode E2 formed by the wall of the cell 1.

The three electrodes E*t*1, ER and E2 are connected to an electric supply source 314 which comprises a potentiostat arranged so as to apply to the control electrode E*t*1 of the enzymatic electrode EE an adjustable potential $E_t$ with respect to the reference electrode ER; the initial value $E_i$ of this potential is empirically established beforehand and set on the supply source 314.

The enzymatic particles pe of the vertically circulating agitated bed are thus alternately brought to different potentials which correspond to $E_t$ and $E_2$ during their successive collisions with the electrodes E*t*1 and E2, respectively.

As may be seen in FIG. 3, the inlet 302 and the outlet 303 are connected to a double-flow metering pump 315. This pump comprises a first inlet connected to a supply reservoir 316, which delivers the liquid reaction system SR via a pipe 317 equipped with a three-way valve 322, and a corresponding first outlet connected to the inlet 302 of the reaction cell 301. The outlet 303 of this cell further comprises a porous partition 318 which prevents passage of the enzymatic particles of the bed and permit passage of liquid from the cell 1, through the outlet 303, to a second inlet of the pump 315, whereof a corresponding second outlet leads to a discharge reservoir 321 via a pump 320 equipped with a three-way valve 323. A by-pass pipe 324 is further connected to these two valves 322 and 323 in order to allow recycling, as will be described further below. The simultaneous actuation of these two valves 322 and 323 is schematically indicated by a broken line.

When the pump 315 is operated during normal operation of the apparatus, this pump delivers a given volume of liquid from the reservoir 316 to the cell 1 and at the same time transfers an equal volume of liquid from this cell 1 to the reservoir 321.

A measuring instrument PR is finally associated with the pipe 320 in order to measure the instantaneous value $P_m$ of an output variable which depends on the reaction rate and corresponds to the reaction product P obtained at the outlet of the apparatus.

This apparatus according to FIG. 3 may be utilized to carry out enzymatic electrocatalysis in the following manner:

a. The suitable enzyme is first selected and the mass ME of enzymatic particles pe is prepared consisting of the enzyme fixed on graphite, as is mentioned above with reference to FIG. 1, for example. However, one may in this case use fine powdered graphite having a mean size between 200 and 400 $\mu$, for example, which allows the fixation ratio (weight ratio enzyme/support) to be further increased, as well as the specific active surface of the whole enzymatic electrode.

b. After having introduced a predetermined amount of enzymatic mass ME into the cell 301 and having assembled the apparatus according to the arrangement shown in FIG. 3, the cell 301 is filled with reaction liquid SR from the reservoir 316, the stirrer 309 is actuated so as to put the particles pe in suspension and form the said agitated bed, and the initial value $E_i$, determined empirically beforehand, is set on the electric supply source 314. The particles pe of the agitated bed in circulation are thus alternately subjected to two potentials which respectively correspond to $E_t$ and $E_2$.

c. During a starting phase of operation of the apparatus, the valves 322 and 323 are adjusted so as to effect recycling of the reaction liquid SR in the cell 301, via the pump 315 and the by-pass pipe 324. Such recycling during the starting phase allows the set value $P_s$ of the output variable to be rapidly attained, as can be determined by measurements with the measuring instrument PR in the liquid recycled in the pipe 324.

d. Once $P_m$ has attained $P_s$, recycling is stopped by switching over the valves 322 and 323 and the throughput of the pump 315 is adjusted to an empirically predetermined value which corresponds to the normal operation of the apparatus; the reaction liquid containing fresh substrate is then continously transferred from the reservoir 316 to the cell 301 to undergo reaction therein while an equal volume of liquid containing the reaction product P (transformed substrate) is discharged from the cell 1 to the reservoir 321.

e. In the course of this normal operation, $P_m$ is continually measured, is compared to $P_s$ in order to determine any difference $\epsilon = P_s - P_m$, and the adjustable potential $E_i$ is increased or decreased accordingly, in such a manner as to annul this difference. In other words, $E_t$ is continually adjusted via the source 314, as a function of $P_m$ as indicated by a broken line connecting PR to 314, in such a manner that $P_m$ is maintained approximately equal to $P_s$. The reaction rate can thus be maintained at a more or less constant value during a long period, thanks to control of $E_t$ so as to maintain an approximately constant enzymatic activity corresponding to $P_s$.

The enzymatic electrocatalysis effect obtained by means of the agitated bed in this apparatus according to FIG. 3 may be explained as follows:

a. The adjustable potential $E_t$ serves to govern the reaction rate by acting on the enzymatic activity. Its initial value $E_i$ is thus selected so that it corresponds to a relatively high level of activity which permits a satisfactory reaction rate to be achieved.

b. Adjustment of the potential $E_t$ then serves to maintain a relatively high level of catalytic activity, corresponding to the desired reaction rate, because it permits rapid compensation of the variations in activity which arise in the course of the reaction and may result either from a change in the properties of the enzyme, or from a change in the reaction conditions, or from both at the same time.

c. Hence, each time that an enzymatic particle collides with the control electrode E*t*1, the enzyme fixed on this particle is subjected to the action of the adjustable potential $E_t$ and then has a relatively high activity corresponding to $E_t$.

d. Now, since the level of $E_t$ is chosen so as to correspond to a relatively high level of activity, the activity of the enzyme will be lower in the absence of the action of $E_t$. Thus, during the relatively long intervals which separate successive collisions of each particle pe with the control electrode de E*t*1, the enzyme fixed on each particle circulating within the agitated bed will be approximately at its open circuit potential (or "OCV") which corresponds to a state of equilibrium of potential with the reaction liquid. At this equilibrium, the level of activity of the enzyme will be relatively low as compared to the activity resulting from the potential $E_t$ which acts intermittently during the said successive collisions. Moreover, the enzymatic activity will likewise be lower during the collisions of each particle pe with the counter-electrode E2, since the potential $E_2$ thereof will correspond to a lower level of activity than said relatively activity resulting from the potential $E_t$.

e. Uniform continuous circulation of the agitated bed, by means of the stirrer 309, nevertheless permits approximately uniform contacting of the particles pe with the electrode E$t$1 and consequently ensures a practically constant catalytic effect due to the action of the adjustable potential $E_t$ on the enzyme fixed to the particles pe of the whole agitated bed.

f. Now, during circulation within the agitated bed, the liquid reaction system is intimately mixed with all of the enzymatic particles undergoing circulation and having a relatively low activity, so that the reaction product, which is formed at the particle surface, may be transferred very rapidly to the bulk of the liquid reaction system within the agitated bed. This intimate mixing likewise ensures that the substrate to be transformed is continuously brought from the bulk of the liquid reaction system to the surface of each particle undergoing circulation in the agitated bed.

g. This circulation of the agitated bed thus permits a relatively high mean catalytic activity to be maintained due to the intermittent action of the potential $E_t$, on one hand, and to the mentioned effects obtained during intimate mixing within the agitated bed. Indeed, thanks to the intermittent reduction of the enzymatic activity, concurrent with said intimate mixing, it is possible to largely obviate undue development of phenomena of competitive inhibition which are liable to seriously hinder the course of the reaction at a high rate. Now, as is known, competitive inhibition of an enzyme may result from a too rapid accumulation of the reaction product, which reduces the reaction rate, in the same way as a rate reduction arising from an excessive variation of the pH of the reaction liquid in contact with the enzyme.

h. Thus, thanks to the combined action of adjusting $E_t$ with agitation of the bed of particles and circulation of liquid by means of the pump 315, it is possible to maintain a high mean reaction rate which is approximately constant during operation of the apparatus of FIG. 3 during relatively long periods.

Figure 4:
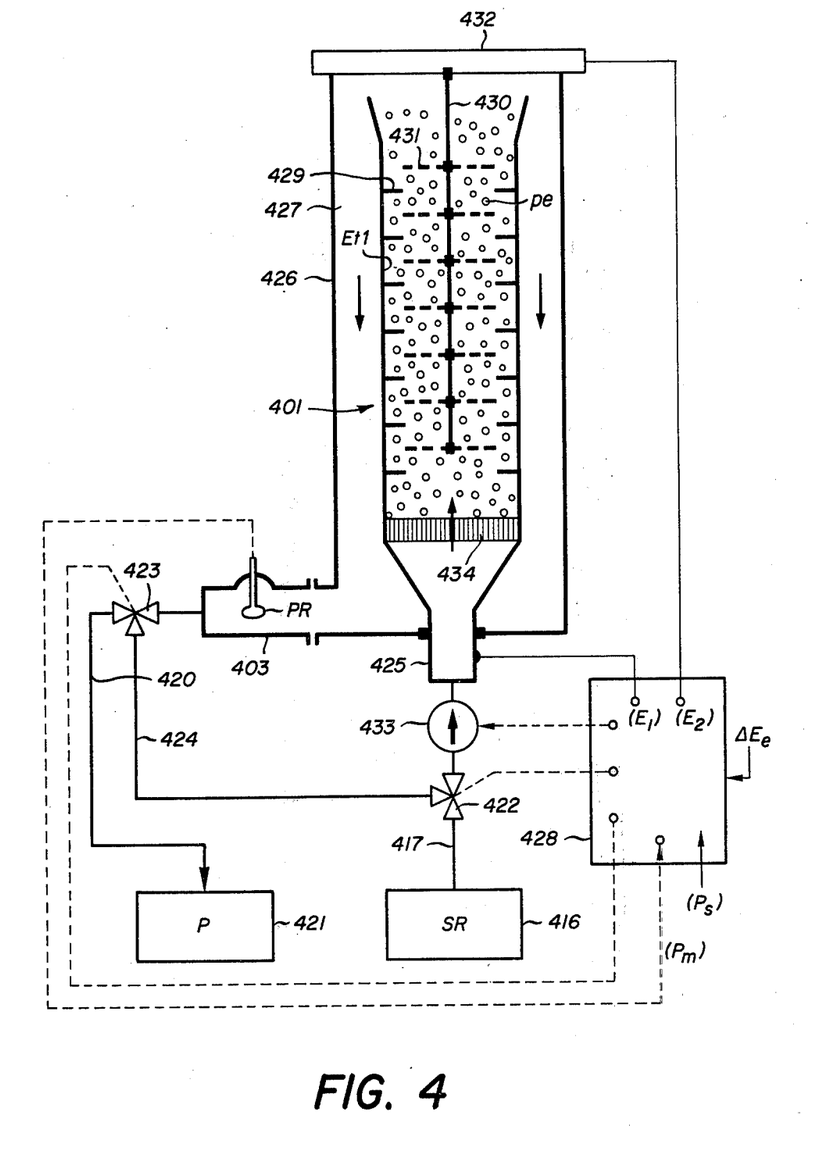
FIG. 4 is a schematic cross-section of a fourth embodiment, which comprises a fluidized bed.

The apparatus according to the embodiment shown in FIG. 4 is provided with an enzymatic electrode comprising an enzymatic mass arranged in the form of a fluidized bed of enzymatic particles pe suspended in an ascending stream of the liquid reaction system passing through a reaction column 401 between an inlet 425 at the bottom and an outlet at the open top end thereof.

A coaxial sleeve 426 surrounds the column 401 so as to define an annular channel 427 which communicates with the open top of the column 401.

A supply reservoir 416 for the liquid reactions system SR, containing the substrate to be transformed, is connected to the inlet 425 via a supply pipe 417 equipped with a three-way valve 422 and pump 433 having an adjustable throughput.

At the bottom end of the column 401, a porous distributor plate 434 is transversely arranged so as to provide passage of a uniform stream of liquid and prevent passage of the particles pe of the fluidized bed.

The wall which laterally defines the column 401 is made of an inert electric conductor (e.g. titanium) and at the same time forms a working electrode E$t$1 of the enzymatic electrode and is connected via the inlet 425 to a terminal ($E_t$) of an electric supply source 428.

The internal surface of this wall of the column 401, which constitutes the electrode E$t$1, is provided with a series of radial baffles 429 in the form of small bars, for example.

The column 1 is further equipped with a counter-electrode E2 which consists of a metallic axial bar 430 (e.g. of titanium) carrying a series of transverse conducting members 431, in the form of grids made of titanium, for example and which is suspended from a conductive covering plate 432, through which the bar 430 is connected to a second terminal ($E_2$) of the supply source 428 via a suitable connection. As appears from FIG. 4, the series of baffles 429 and the conducting members 431 are in a staggered arrangement, in such a manner that the ascending liquid has, on one hand, an approximately uniform vertical velocity which enables maintenance of the fluidized bed of particles pe in suspension within the column. On the other hand, this arrangement serves to deviate the ascending liquid alternately outwards towards the column wall forming the electrode E$t$1 and inwards towards the counter-electrode E2 (430,431).

The particles of the fluidized bed may be prepared from powdered or granular graphite to which the selected enzyme is fixed in any appropriate manner, such as described further above, for example.

The porosity (liquid / solid ratio by volume) of the fluidized bed may be about 0.65.

By utilizing well known fluidization techniques, the mean size of the particles pe may be selected from the range between 400 and 1500 $\mu$ and the velocity of the ascending liquid may be selected as a function of this size, in such a manner as to form the fluidized bed, to maintain it within the column 401 and to prevent the particles pe from being carried away out of the column.

The liquid coming out of the fluidized bed at the open upper end of the reaction column 401 flows into the channel 427 where it circulates downwards and passes to the outlet 403.

The outlet 403 contains a measuring instrument PR and is connected to a reservoir 421 for the reaction product P via a conduit 420 equipped with a three-way valve 423. This valve 423 further allows the outlet 403 to be connected to the inlet 425 via a by-pass pipe 424 leading to the valve 422, in order to thus allow recycling in the column 401.

The electric supply source 428 is arranged to apply between the electrodes E$t$1 and E2 an adjustable potential difference $\Delta E_{t-2} = E_t - E_2$ with an initial value $\Delta E_i$ which is predetermined empirically, is set on the source 428 and corresponds to an initial potential $E_i$ of the control electrode E$t_t$ with respect to a reference electrode not shown in FIG. 4.

As in the preceding case, the source 428 allows setting of the set value $P_s$ of an output variable P and control of $\Delta E_{t-2}$ as a function of the difference $\epsilon$ between $P_s$ and a value $P_m$ measured by the instrument PR.

The described apparatus according to FIG. 4 may serve to carry out the invention in the following manner:

a. After having introduced an appropriate mass of enzymatic particles pe into the column 401, the apparatus is assembled according to FIG. 4, the values $\Delta E_i$ and $P_s$ are set on the source 428 and the pump 433 is operated with a throughput which is predetermined empirically, so that the liquid reaction system SR coming from the reservoir 416 circulates upwards in the column 401 with a predetermined speed of ascension allowing a fluidized bed to be formed and maintained in the column.

b. Enzymatic electrocatalysis of the desired reaction is achieved by means of the mass of particles of this fluidized bed and the treated liquid containing the reaction product P passes through the channel 427 to the outlet 403 from which it is conducted by the valve 428 to the conduit 420 which leads it to the reservoir 421.

c. Now, the particles pe of the fluidized bed come alternately into collision with the electrodes E$t$1 and E2 (430, 431) and their enzymatic activity will depend essentially on the potential $E_i$ applied to the control electrode E$t$1 by the source 428.

d. While the reaction proceeds in the column 401, $P_m$ is measured by means of the instrument PR, each divergence $\epsilon$ is determined which appears between $P_m$ and $P_s$ and $\epsilon E_{i-2}$ is controlled as a function of this divergence, by means of the source 428, in such a manner as to maintain $P_m$ approximately equal to $P_s$.

e. The desired mean reaction corresponding to the set value $P_s$ is thus maintained thanks to control of $\Delta E_{i-2}$ in combination with the action of the fluidized bed. Indeed, as in the case of the agitated bed according to FIG. 3, the fluidized bed according to FIG. 4 permits the enzyme fixed to each particle pe to be subjected to brief periods of relatively high activity during its successive collisions with the control electrode E$t$1, with intermediate periods of relatively reduced activity when the particle is not subjected to the action of the potential $E_i$ of this electrode. Moreover, the enzymatic particles pe of the fluidized bed likewise undergo very intimate mixing with the liquid reaction system SR, whereby a similar result may be ensured and the development of competitive inhibition phenomena may likewise be avoided.

The use of such a fluidized bed enables the utilization, in a both simple and efficient manner, of a relatively large mass of enzymatic particles associated with the enzymatic electrode, by dimensioning the column 401 accordingly. In addition, the fluidized bed allows uniform flow of the liquid reaction system SR to be obtained, and regular progression thereof through the fluidized bed, whereby notable back-mixing of liquid having undergone various stages of reaction may be avoided. This allows, in particular, the development of competitive inhibition phenomena to be avoided, which are due to the presence of the reaction product P in the liquid in contact with the enzyme and can considerably affect the enzymatic catalysis of certain reactions.

Now, switching over the valves 422 and 423 allows recycling of the liquid through the column 401, for example, during an initial starting phase for rapidly attaining a value $P_m - P_s$, as has been described with reference to FIG. 3, before proceeding to continuous operation where the liquid leaving the column 401 is discharged directly to the reservoir 421. This recycling may on the other hand be envisaged for the normal operation of the apparatus according to FIG. 4, in alternation with intermediate phases for discharging liquid to the reservoir 421 and supplying the column 401, from the reservoir 416, with liquid SR containing fresh substrate to be transformed.

The electric supply source 428 may, alternatively, comprise a potentiostat and be associated with a reference electrode situated in the column 401. An adjustable potential $E_i$ is then applied to the electrode E$t$1 with respect to this reference electrode, as in the case of the apparatus according to FIG. 3.

It is evident that one may utilize various variants of the embodiments described above. Thus, for example, the solid, fixed, inert working electrode associated with the enzymatic mass may be given any configuration for a satisfactory triple electrical contact and an appropriate relative movement between the liquid reaction system, the particulate enzymatic mass and the working electrode. The inert counter-electrode may moreover have any appropriate form and relative arrangement with respect to the enzymatic electrode.

The said relative movement may moreover be effected in various ways. Thus, for example, as a variant of the described fluidized bed maintained in a fixed general position in the reaction chamber, a suspension of the enzymatic particles in the liquid reaction system may be circulated so that each particle in suspension circulates through the reaction chamber and is thereby subjected to intermittent contact with the inert working electrode by repeatedly colliding therewith, either in a single passage, or in several successive passages (by recycling) of each particle through the reaction chamber.

The following examples further illustrate the application of the method in accordance with the present invention.

EXAMPLE 1

Defatted and deproteinized lactoserum is subjected to hydrolysis catalyzed by lactase for transforming the lactose to glucose and galactose in the apparatus according to FIG. 2.

The enzymatic electrode here comprises a mass of enzymatic particles performed of graphite particles (mean particle size 1,500 $\mu$) carrying the enzyme lactase and forming a porous packed bed arranged in contact with the working electrode E$t$1. The lactoserum to be hydrolyzed is supplied to the reaction cell 201 under approximately constant initial conditions (flow rate, composition, temperature, pH) which are predetermined empirically. In the present case, the initial lactose content of the lactoserum was 45 gr/liter, the initial temperature was 25° C and the initial pH was equal to 6.5.

The enzymatic electrode is in this case subjected to a periodic, positive polarization by applying to the working electrode E$t$1 a potential $E_i$ which alternates initialy between + 900 m V/SCE and + 300 m V/SCE ($E_i = +$ 600 m V/SCE).

The mean value of the potential $E_i$ applied in the form of periodic pulse series (with a frequency of 1 Hz) is then adjusted as a function of the glucose content $P_m$ measured in the liquid passing through the outlet 203 so as to maintain a substantially uniform glucose content corresponding to the desired set value $P_s$, which was set at 13.5 gr/liter in the present case.

This periodic variation of $E_i$ and the adjustment of its mean value enable a relatively high mean enzymatic activity to be maintained which corresponds to an approximately constant reaction rate and thus delivers a product presenting a uniform composition, i.e. uniform glucose and galactose contents.

A gain of activity of 50% was obtained by applying the adjustable, periodically varying potential $E_t$ in the present case.

EXAMPLE 2

The hydrolysis of lactoserum is effected as in Example 1, but by means of an apparatus according to FIg. 3, which comprises an enzymatic electrode with an agitated bed.

This electrode is likewise polarized positively in this case and the initial value $E_i$ (predetermined experimentally) of the potential $E_t$ applied to the electrode E$t$1 is then of the order of + 1,100 m V/SCE. The value of $E_t$ is then adjusted as a function of $P_m$ so as to maintain a relatively high mean catalytic activity which provides a uniform treated product as in Example 1.

In the present case, the gain of activity due to the application of $E_t$ amounted to 100%. In addition, a 100% hydrolysis was achieved.

It is understood that enzymatic electrocatalysis effected in accordance with the invention is applicable to practically all reactions catalyzed by an enzyme and may be carried out in any type of apparatus comprising an appropriate enzymatic electrode which permits adjustment of the potential of the support of the fixed enzyme.

The values of $E_t$ may likewise differ notably from those given above. The frequency of the periodic potential pulse trains may have any appropriate value and the pulses may have different forms (square, triangular, etc).

As appears from the foregoing, the present invention allows heterogeneous enzymatic catalysis to be effected in a controlled manner so as to be able to meet all requirements of an industrial process.

Indeed, this invention allows several important technical advantages to be combined, such as:

i. maximum active suface per unit electrode volume is obtained, the surface available for fixation of the enzyme on all of the particles and hence for utilizaton thereof to achieve controlled catalysis being extremely large;

ii. very efficient utilization of the large total active surface of the enzyme fixed to the particles thanks to the intimate contact obtained by means of the relative movement between the liquid reaction medium or system and the enzymatic particles;

iii. ready control of the catalytic activity thanks to an adjustable electric polarization of each enzymatic particle;

iv. possibility of maintaining a satisfactory mean enzymatic activity thanks to an alternating variation of the potential of the enzymatic support, during which:

a. the enzyme on one hand presents a high activity obtained by intermittent and adjustable polarization so as to enable compensation of variations of activity whatever their cause may be ageing, variable reaction conditions, etc.);

b. the enzyme presents a relatively reduced activity during the intermediate intervals enable the evolution of competitive inhibition phenomena to be largely obviated.

What we claim is:

1. A method of governing the reaction rate of enzymatic reactions for continuously transforming a substrate by contact with an enzyme fixed to a solid carrier, comprising the steps of: bringing an electrically conductive liquid reaction system, containing at least one substrate to be transformed, into contact with an enzymatic electrode comprising at least one enzyme fixed to an electrically conductive solid support medium; and regulating the catalytic activity of said enzyme by applying an electric potential to said support medium while adjusting the value of said potential so as to transform said substrate at a given rate, said method further comprising the improvements consisting of:

a. providing said enzymatic electrode with a solid, inert, working electrode and with a particulate mass of discrete enzymatic particles, each formed essentially of said conductive support medium having said enzyme fixed to the surface thereof;

b. placing said enzymatic electrode in a reaction space wherein said particulate mass of enzymatic particles is arranged for electrical contact thereof with said working electrode;

c. circulating said liquid reaction system within said reaction space; and d. applying said adjustable potential, via said working electrode, to the conductive support medium of said enzymatic particles.

2. The method of claim 1 wherein said particulate mass of enzymatic particles consists of graphite particles having a mean size lying between 0.4 and 1.5 mm, with said enzyme fixed to the surface thereof.

3. The method according to claim 1 wherein said working electrode is subjected to continuous movement in a loose bed of said enzymatic particles whereby to cause agitation of said bed to provide continually repeated direct contact of all particles therein with said working electrode.

4. A method of governing the reaction rate of enzymatic reactions for continuously transforming a substrate by contact with an enzyme fixed to a solid carrier, comprising the steps of: bringing an electrically conductive liquid reaction system, containing at least one substrate to be transformed, into contact with an enzymatic electrode comprising at least one enzyme fixed to an electrically conductive solid support medium; and regulating the catalytic activity of said enzyme by applying an electric potential to said support medium while adjusting the value of said potential so as to transform said substrate at a given rate, said method further comprising the improvements consisting of:

applying to said support medium a variable potential alternating between two levels, while adjusting the mean value thereof so as to provide a corresponding mean catalytic activity of said enzyme for transforming said substrate at a given rate.

5. A method of governing the reaction rate of enzymatic reactions for continuously transforming a substrate by contact with an enzyme fixed to a solid carrier, comprising the steps of: bringing an electrically conductive liquid reaction system, containing at least one substrate to be transformed, into contact with an enzymatic electrode comprising at least one enzyme fixed to an electrically conductive solid support medium; and regulating the catalytic activity of said enzyme by applying an electric potential to said support medium while adjusting the value of said potential so as to transform said substrate at a given rate, said method further comprising the improvements consisting of:

a. providing said enzymatic electrode with a solid inert working electrode and with a particulate mass of discrete enzymatic particles, each formed essentially of said conductive support medium having said enzyme fixed to the surface thereof;

b. placing said enzymatic electrode in a reaction space wherein said particulate mass of enzymatic particles is arranged for electrical contact thereof with said working electrode;

c. circulating said liquid reaction system within said reaction space; and d. applying an alternating potential via said working electrode to the support medium of said enzymatic particles, while adjusting the mean value of said potential so as to provide a corresponding mean catalytic activity of said enzyme fixed to said particles, whereby to transform said substrate at a given rate.

6. The method of claim 5 wherein said particulate mass of enzymatic particles is arranged to form a fixed porous bed in contact with said working electrode, said liquid reaction system being continuously circulated through said fixed bed within said reaction space, and said alternating potential being applied to the working electrode and thereby applied to the support medium of the enzymatic particles of said fixed bed.

7. A method of governing the reaction rate of enzymatic reactions for continuously transforming a substrate by contact with an enzyme fixed to a solid carrier, comprising the steps of: bringing an electrically conductive liquid reaction system, containing at least one substrate to be transformed, into contact with an enzymatic electrode comprising at least one enzyme fixed to an electrically conductive solid support medium; and regulating the catalytic activity of said enzyme by applying an electric potential to said support medium while adjusting the value of said potential so as to transform said substrate at a given rate, said method further comprising the improvements consisting of:

a. providing said enzymatic electrode with a solid, inert, working electrode and with a particulate mass of discrete enzymatic particles each formed essentially of said conductive support medium having said enzyme fixed to the surface thereof;

b. placing said enzymatic electrode in a reaction space wherein said particulate mass is arranged to provide an agitated bed of said enzymatic particles whereby to provide repeated contact thereof with said working electrode;

c. circulating said liquid rection system in said reaction space so as to provide said agitated bed of enzymatic particles in suspension in said liquid system, whereby each suspended particle in said agitated bed undergoes continually repeated impingements on said working electrode; and d. applying said adjustable potential to said working electrode so as to thereby apply said potential to the support medium of each suspended enzymatic particle by intermittent contact thereof during said continually repeated impingements thereof on said working electrode, each said suspended particle being at a different potential level while undergoing movement within said agitated bed, between successive impingements thereof on said working electrode.

8. The method of claim 7, wherein said liquid reaction system is subjected to a circulating movement by means of a stirring member providing said agitated bed within said reaction space, said space further having an inert counter-electrode arranged therein, whereby the suspended particles in said agitated bed undergo successive impingement on said counter-electrode, alternating with said successive impingements thereof on said working electrode.

9. The method of claim 7 wherein said agitated bed is provided in the form of a fluidized bed of said enzymatic particles in suspension in an ascending stream of said liquid reaction system circulating through said reaction space.

10. An apparatus for governing the reaction rate of an enzymatic reaction for continuously transforming a substrate contained in an electrically conductive liquid system, comprising:

a. at least one enzymatic electrode having at least one enzyme fixed to the surface of a solid, electronically conductive support associated with means for applying an adjustable potential to said electrode;

b. a reaction chamber which is equipped with an enzymatic electrode and with an inert counter-electrode and is adapted to receive said liquid reaction system and to discharge the products of the enzymatic reaction; and c. adjustable electrical supply and voltage control means connected to said enzymatic electrode and to said counterelectrode and adapted to apply between said electrodes a potential difference which is adjustable so as to regulate the catalytic activity of said enzyme; the improvement wherein:

said enzymatic electrode comprises a particulate enzymatic mass, composed of discrete enzymatic particles, each essentially formed of said solid conductive support having said enzyme fixed thereto, and further comprises a solid, inert working electrode, operatively associated with said mass and with said electrical supply and voltage control means, so as to subject the particles of said mass to an adjustable potential;

said apparatus further comprises circulating means adapted to circulate said liquid reaction system within said reaction chamber so as to provide intimate contact thereof with each particle of said enzymatic mass, the particles of said mass being subjected to said adjustable potential during said circulation.

11. The apparatus of claim 10 wherein said electrical supply and voltage control means are arranged to apply to said working electrode a potential which varies periodically between two potential levels and to adjust the mean value of said two potential levels, so as to thereby regulate the activity of said enzyme.

12. The apparatus of claim 10 wherein said enzymatic mass constitutes a porous fixed bed of said particles arranged in contact with said working electrode.

13. The apparatus of claim 10 further comprising a stirring device, arranged to form an agitated bed of said enzymatic particles in suspension in said liquid reaction system and to thereby produce continually repeated collisions of the particles of the agitated bed with said working electrode.

14. The apparatus of claim 10 wherein the said circulating means are arranged to produce an ascending stream of said liquid reaction system passing through said reaction chamber at an adjustable speed, to allow formation of a fluidized bed of said enzymatic particles and to thereby provide continually repeated collisions of each particle of the fluidized bed with said working electrode.

* * * * *